US00PP14793P2

(12) United States Plant Patent
Oudshoorn

(10) Patent No.: US PP14,793 P2
(45) Date of Patent: May 18, 2004

(54) VERBASCUM PLANT NAMED 'BUTTERCUP'

(50) Latin Name: *Verbascum hybrida*
Varietal Denomination: Buttercup

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 10/437,958

(22) Filed: May 13, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A distinct cultivar of Verbascum plant named 'Buttercup', characterized by its upright plant habit; freely flowering habit; and large yellow-colored flowers.

1 Drawing Sheet

Botanical classification/cultivar designation: *Verbascum hybrida* cultivar Buttercup.

BACKGROUND OF THE INVENTION

The present Invention relates to a new and distinct cultivar of Verbascum plant, botanically known as *Verbascum hybrida,* and hereinafter referred to by the cultivar name Buttercup.

The new Verbascum plant originated from a chance cross-pollination of two unidentified selections of *Verbascum hybrida,* not patented. The new Verbascum was discovered by the Inventor in 2000 in a controlled environment in Rijpwetering, The Netherlands. Plants of the new Verbascum differed primarily from plants of the unidentified parental selections and other Verbascum cultivars known to the Inventor in flower size and coloration.

Asexual reproduction of the new cultivar by divisions in a controlled environment in Rijpwetering, The Netherlands, has shown that the unique features of this new Verbascum are stable and reproduced true to type in successive generations.

SUMMARY OF THE INVENTION

Plants of the cultivar Buttercup have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'Buttercup'. These characteristics in combination distinguish 'Buttercup' as a new and distinct cultivar:

1. Upright plant habit.
2. Freely flowering habit.
3. Large yellow-colored flowers.

BRIEF DESCRIPTION OF THE PHOTOGRAPH

The accompanying colored photograph illustrates the overall appearance of the new Verbascum, showing the colors as true as it is reasonably possible to obtain in colored reproductions of this type. Colors in the photograph may differ slightly from the color values cited in the detailed botanical description which accurately describe the colors of the new Verbascum. The photograph comprises a side perspective view of a typical flowering plant of 'Buttercup' grown in a container.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photograph and for the following description were grown for about one year under outdoor field conditions which closely approximate commercial production conditions in Lisserbroek, The Netherlands. During the production of the plants, day temperatures ranged from 14 to 30° C. and night temperatures ranged from 7 to 16° C. The photographs and description were taken in July, 2002.

Botanical classification: *Verbascum hybrida* cultivar Buttercup.

Parentage: Chance cross-pollination of two unidentified selections of *Verbascum hybrida,* not patented.

Propagation:
- *Type.*—By divisions.
- *Root description.*—Fibrous, fleshy, thick; whitish in color.

Plant description:
- *Form.*—Perennial flowering plant; upright plant habit; narrow inverted triangle; vigorous growth habit.
- *Plant height.*—About 85 cm.
- *Plant diameter.*—About 35 cm.
- *Basal stem description.*—Length: About 85 cm. Diameter: About 6 mm. Internode length: About 4.2 cm. Strength: Strong. Texture: Pubescent. Color: 143A to 143B.
- *Foliage description.*—Arrangement: Alternate, simple. Length, lower leaves: About 20 cm. Width, lower leaves: About 6.2 cm. Shape: Narrowly ovate to lanceolate. Apex: Obtuse to broadly acute. Base: Cordate. Margin: Crenate. Texture, upper and lower surfaces: Pubescent; rugose. Venation pattern: Pinnate. Color: Young foliage, upper surface: Between 137A and 143A. Young foliage, lower surface: 138A to 138B. Fully expanded foliage, upper surface: Between 137A and 141A. Fully expanded foliage, lower surface: 138A. Venation, upper and lower surfaces: 144D. Petioles: Length: About 9.5 cm. Diameter: About 3.5 mm. Color: 144D. Leaflets: Quantity per petiole: About five. Length: About 1.5 cm. Width: About 1 cm. Shape: Ovate. Texture, upper and lower surfaces: Pubescent. Color: Same as leaf coloration.

Flower description:

*Appearance.*—Single rotate flowers with five petals arranged on terminal racemes. Flowers slightly cupped and face mostly outwardly. Flowers not persistent.

*Quantity of flowers.*—Freely flowering habit, about 50 flowers develop per raceme.

*Natural flowering season.*—Plants flower continuously from July to August in The Netherlands.

*Fragrance.*—None detected.

*Flower longevity.*—About five days.

*Inflorescence length.*—About 30 cm.

*Inflorescence diameter.*—About 5.9 cm.

*Flower diameter.*—About 4.8 cm.

*Flower depth (height).*—About 2.3 cm.

*Flower buds.*—Length: About 1.1 cm. Diameter: About 1.2 cm. Shape: Flattened globular. Color: Towards the apex, 6A; towards the base, 4A.

*Petals.*—Quantity per flower: Five; fused at the base. Arrangement: Rotate, slightly overlapping. Length, upper and lower petals: About 2.2 cm. Width, upper two petals: About 1.8 cm. Width, lower three petals: About 2.2 cm. Shape: Orbicular to broadly ovate. Apex: Rounded. Base: Attenuate. Margin: Entire. Texture, upper and lower surface: Smooth, glabrous. Color: Upper petals: When opening and fully opened, upper surface: 6B; two basal spots, 187A. When opening and fully opened, lower surface: 6B. Lower petals: When opening and fully opened, upper surface: Towards the apex, 4A; towards the base, 4C. When opening and fully opened, lower surface: Towards the apex, 4A; towards the base, 4C.

*Sepals.*—Quantity per flower: Five, fused at base. Arrangement: Rotate, star-shaped. Length: About 1.1 cm. Width: About 3 to 7 mm. Shape: Elliptic to narrowly lanceolate. Apex: Acute. Base: Cuneate, fused. Margin: Serrate. Texture, upper and lower surfaces: Pubescent. Color: Upper surface: Towards the apex, 143B; towards the base, 143C. Lower surface: 143A.

*Peduncles.*—Length: About 85 cm. Diameter: About 5 mm. Angle: Erect. Strength: Strong. Color: 143A to 143B.

*Pedicels.*—Length: About 5 mm. Diameter: About 1.2 mm. Angle: About 45° from vertical. Strength: Strong. Color: 143A to 143B.

*Reproductive organs.*—Stamens: Quantity per flower: Four. Anther shape: Narrowly oblong. Anther length: About 7 mm. Anther color: 23A. Pollen amount: Scarce. Pollen color: 17A to 17B. Pistils: Quantity per flower: One. Style length: About 2.5 cm. Style color: 199D. Stigma shape: Club-shaped, narrow. Stigma color: 196D. Ovary color: 143C to 143D.

*Fruit.*—Quantity per flower: One. Length: About 9 mm. Diameter: About 6 mm. Texture: Smooth, glabrous. Color: 199A to 199B.

*Seed.*—Length: About 1 mm. Diameter: About 0.5 mm. Color: 199B to 199C.

Disease/pest resistance: Plants of the new Verbascum have not been noted to be resistant to pathogens or pests common to Verbascum.

Temperature tolerance: Plants of the new Verbascum are tolerant to temperatures from about −20 to 40° C.

It is claimed:

1. A new and distinct cultivar of Verbascum plant named 'Buttercup', as illustrated and described.

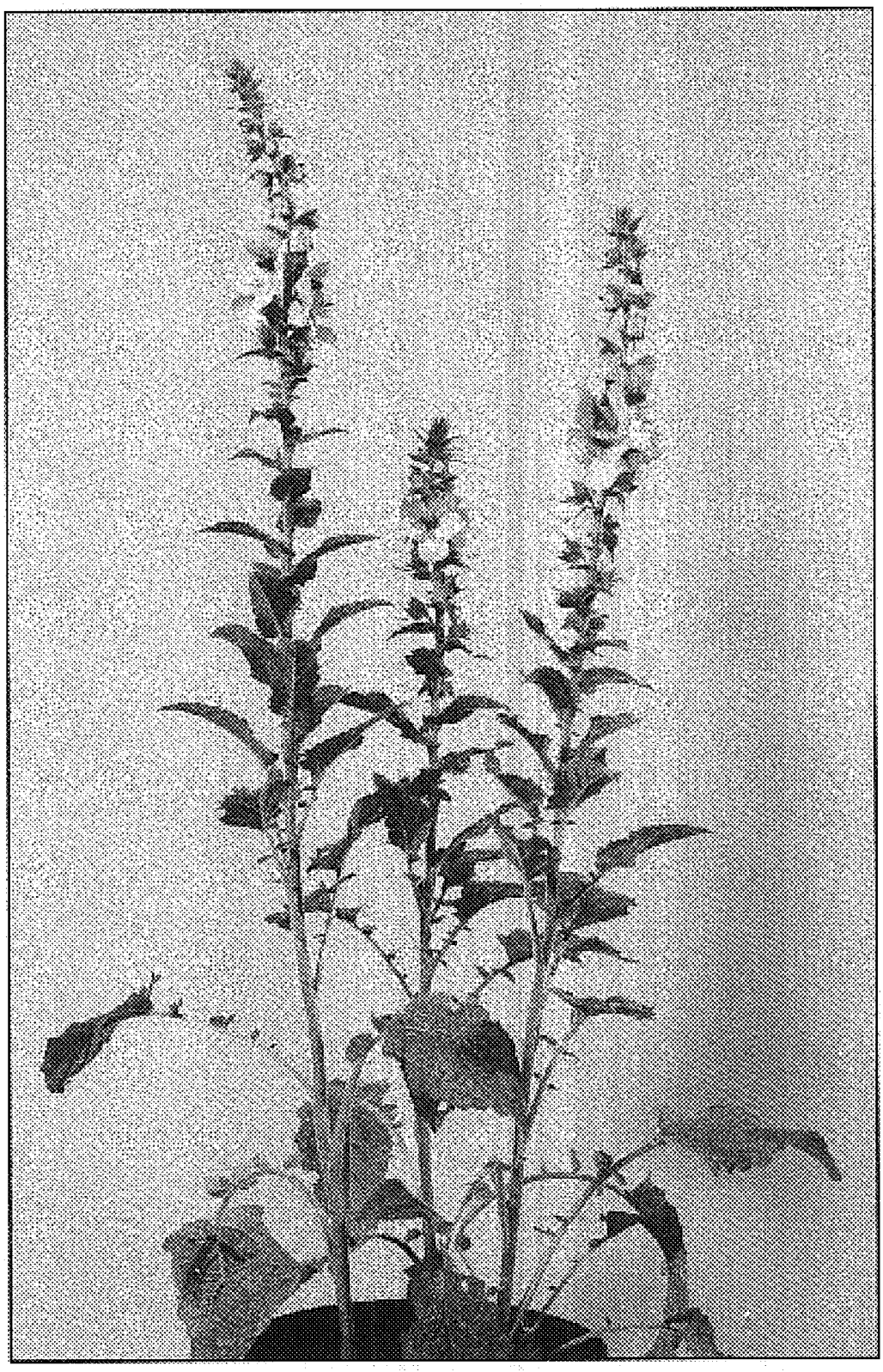

* * * * *